United States Patent
Long et al.

(10) Patent No.: US 11,999,981 B2
(45) Date of Patent: Jun. 4, 2024

(54) AGARASE MUTANT WITH IMPROVED THERMAL STABILITY AND APPLICATION THEREOF

(71) Applicant: Jiangnan University, Wuxi (CN)

(72) Inventors: Jie Long, Wuxi (CN); Ziying Ye, Wuxi (CN); Zhengyu Jin, Wuxi (CN); Cheng Lu, Wuxi (CN); Xingfei Li, Wuxi (CN); Yaoqi Tian, Wuxi (CN); Yuxiang Bai, Wuxi (CN); Xing Zhou, Wuxi (CN); Chao Qiu, Wuxi (CN); Long Chen, Wuxi (CN); Zhengjun Xie, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 0 days.

(21) Appl. No.: 18/489,954

(22) Filed: Oct. 19, 2023

(65) Prior Publication Data
US 2024/0060062 A1  Feb. 22, 2024

Related U.S. Application Data

(63) Continuation of application No. PCT/CN2022/126972, filed on Oct. 24, 2022.

(30) Foreign Application Priority Data

Apr. 8, 2022  (CN) .......................... 202210367163.8

(51) Int. Cl.
  *C12N 9/38*   (2006.01)
  *C12N 15/63*  (2006.01)

(52) U.S. Cl.
  CPC .......... *C12N 9/2468* (2013.01); *C12N 15/63* (2013.01); *C12Y 302/01081* (2013.01)

(58) Field of Classification Search
  CPC .................................................. C12N 9/2468
  See application file for complete search history.

(56) References Cited

FOREIGN PATENT DOCUMENTS

| CN | 109072268 A | 12/2018 |
| CN | 109207459 A | 1/2019 |
| CN | 111544437 A | 8/2020 |
| CN | 114836405 A | 8/2022 |

OTHER PUBLICATIONS

Pluvinage et al., "Substrate Recognition and Hydrolysis by a Family 50 exo-beta-Agarase, Aga50D, from the Marine Bacterium Saccharophagus degradans", The Journal of Biological Chemistry vol. 288, No. 39, pp. 28078-28088, Sep. 27, 2013.*
Guo, yuxi et al. "Improving Thermal Stability of Microbulbifer sp. AG1 Agarase Based on Rational Design" Journal of Chinese Institute of Food Science and Technology, vol. 19 No. 12, Dec. 31, 2019.
Bing-Mei Su et al., "Mutagenesis on the surface of a -agarase from Vibrio sp. ZC-1 increased its thermo-stability", Enzyme Microb Technol, vol. 127, Apr. 6, 2019.
Weiner R.M et al., "b-agarase [Saccharophagus degradans 2-40]" GenBank ID: ABD81904. GenBank, Feb. 10, 2014.
Min-Kyung Jang et al. "Enhancement of the thermostability of a recombinant b-agarase, AgaB, from Zobellia galactanivorans by random mutagenesis" Biotechnol Lett 32: 943-949, Mar. 8, 2010.
Chao Shi et al. "Enhancing the Thermostability of a Novel -agarase AgaB through Directed Evolution" Appl Biochem piotechnol 151: 51-59, Mar. 4, 2008.
Pujuan Zhang et. al. "Structure-based design of agarase AgWH50C from Agarivorans gilvus WH0801 to enhance thermostability" Applied microbiology and biotech, Dec. 6, 2018.

* cited by examiner

Primary Examiner — Suzanne M Noakes
(74) Attorney, Agent, or Firm — IPRO, PLLC

(57) ABSTRACT

Disclosed are an agarase mutant with improved thermal stability and application thereof, belonging to the fields of genetic engineering technology and enzyme engineering. The present disclosure provides an agarase mutant, which is obtained by mutating the amino acid at the $86^{th}$ site, the $373^{rd}$ site, the $374^{th}$ site, the $496^{th}$ site, the $507^{th}$ site, or the $747^{th}$ site of agarase with an amino acid sequence as shown in SEQ ID NO. 1. The agarase mutant provided by the present disclosure improves the thermal stability and the hydrolytic activity of the agarase. Compared with the wild type enzyme, the mutant enzyme shows excellent heat resistance and can be industrially used at a relatively high temperature, so that the utilization rate of agar raw materials and the yield of oligosaccharides from agar are improved, and the mutant enzyme has a good industrial application prospect.

4 Claims, 6 Drawing Sheets

Specification includes a Sequence Listing.

SEQUENCE LISTING

```
Sequence total quantity: 28
SEQ ID NO: 1            moltype = AA   length = 793
FEATURE                 Location/Qualifiers
source                  1..793
                        mol_type = protein
                        organism = synthetic construct
SEQUENCE: 1
MGAIGGLVKI NISFIPLFVI SASIFIGACN SSKLESGVDS NNISPVMLFD FENDQVPSNI   60
HFLNARASIE TYTGINGEPS KGLKLAMQSK QHSYTGLAIV PEQPWDWSEF TSASLYFDIV  120
SVGDHSTQFY LDVTDQNGAV FTRSIDIPVG KMQSYYAKLS GHDLEVPDSG DVNDLNLASG  180
LRSNPPTWTS DDRQFVWMWG VKNLDLSGIA KISLSVQSAM HDKTVIIDNI RIQPNPPQDE  240
NFLVGLVDEF GQNAKVDYKG KIHSLEELHA ARDVELAELD GKPMPSRSKF GGWLAGPKLK  300
ATGYFRTEKI NGKWMLVDPE GYPYFATGLD IIRLSNSSTM TGYDYDQATV AQRSADDVTP  360
EDSKGLMAVS EKSFATRHLA SPTRAAMFNW LPDYDHPLAN HYNYRRSAHS GPLKRGEAYS  420
FYSANLERKY GETYPGSYLD KWREVTVDRM LNWGFTSLGN WTDPAYYDNN RIPFFANGWV  480
IGDFKTVSSG ADFWGAMPDV FDPEFKVRAM ETARVVSEEI KNSPWCVGVF IDNEKSFGRP  540
DSDKAQYGIP IHTLGRPSEG VPTRQAFSKL LKAKYKTIAA LNNAWGLKLS SWAEFDLGVD  600
VKALPVTDTL RADYSMLLSA YADQYFKVVH GAVEHYMPNH LYLGARFPDW GMPMEVVKAA  660
AKYADVVSYN SYKEGLPKQK WAFLAELDKP SIIGEFHIGA MDHGSYHPGL IHAASQADRG  720
EMYKDYMQSV IDNPYFVGAH WFQYMDSPLT GRAYDGENYN VGFVDVTDTP YQEMVDAAKE  780
VNAKIYTERL GSK                                                    793

SEQ ID NO: 2            moltype = DNA   length = 2256
FEATURE                 Location/Qualifiers
source                  1..2256
                        mol_type = other DNA
                        organism = synthetic construct
SEQUENCE: 2
ggatccatgt tattcgattt tgaaaacgat caagtccctt caaatattca tttttttaaat    60
gcgcgtgcaa gtatagaaac ctataccggt ataaatgcgg agccgagtaa agggttaaag   120
ttggcgatgc agtccaagca gcacagttat actggccttg ccattgtgcc agagcagcct   180
tgggattgga gcgagtttac ctctgctagc ttgtatttcg atatagtcag tgttggcgat   240
cattccacac aatttttattt agatgttacc gaccaaaatg gcgccgtgtt tacccgcagt   300
attgatattc cagtgggtaa aatgcaatcg tactacgcca agttaagcgg tcacgattta   360
gaagtgcccg atagtggaga cgttaacgat ttaaacctcg cctctggctt gcgttctaac   420
ccgcctacat ggacatctga cgataggcag tttgttttgga tgtggggagt gaaaaattta   480
gatttgtcgg gcattgctaa aatatcgcta agtgtgcaaa gcgcaatgca cgataaaaca   540
gttattatcg ataatattcg tattcaaccc aacccgccgc aagatgaaaa cttccttgtc   600
ggtttggtag acgagtttgg ccaaaacgcc aaagttgatt acaagggtaa aatccatagt   660
ttagaagaat tgcatgcagc gcgcgatgtg gaactggccg agcttgatgg caagccaatg   720
cctagtcgct ctaagtttgg cggttggttg gccggccccca agctaaaagc tacagggtac   780
tttcgcacag aaaaaattaa cggtaaatgg atgctagtag acccagaagg gtacccttac   840
tttgctacgg gtttagacat tattcgccta tctaattcat ctaccatgac tggttacgat   900
tacgatcaag ctactgttgc tcagcgctct gccgacgatg taacacctga agactcaaaa   960
ggtttaatgg cagtgagcga aaaatcattt gctacgcgcc acctagcatc gccaacacga  1020
gcggcaatgt ttaactggtt gccagattac gatcaccctc tgcaaatca ttataactac  1080
cgtcgctctg cgcattccgg cccactgaaa cgcggtgaag cctacagctt ctacagtgcc  1140
aaccttgagc gtaaatacgg tgaaacttac cccggttctt acttggataa gtggcgcgaa  1200
gtaacggtag acagaatgct aaactgggcc tttacctcgc taggcaactg gactgaccca  1260
gcatattacg acaacaatcg cataccgttt ttcgcgaatg gtttgggtaat aggggatttt  1320
aaaaccgtat ctagcggtgc ggattttttgg ggcgcaatgc cagatgtatt cgacccagaa  1380
tttaaagtgc gcgctatgga aacggcacgc gtggtttcag aagaaattaa aaatagccct  1440
tggtgcgtag gggtatttat cgataacgaa aaaagcttcg gtcgccccga ttccgataag  1500
gcgcaatacg gtattcccat tcataccctc ggtcgcccaa gcgaaggtgt gcctactagg  1560
caggcgttta gtaagctgct taaagccaaa tacaaaacta tagccgcgtt aaacaatgcc  1620
tggggttaa agcttagttc ttgggctgag tttgatttgg gcgtagatgt aaaagcgctg  1680
ccggtaaccg atactctgcg cgcagattac tcaatgttac tttcggccta tgcggaccaa  1740
tattttaagg tggtacacgg cgcggttgaa cattacatgc cgaaccactt gtatttaggc  1800
gcacgctttc ctgattgggg aatgccaatg gaggtagtga agctgccgc aaaatacgcc  1860
gatgtggtta gctataattc ctacaaagag ggcttgccta agcagaagtg ggcttttttta  1920
gcagagctag ataagccgag tataatcggt gagtttcaca taggtgctat ggatcacggt  1980
tcgtatcacc ccggttttaat tcacgctgcg tcgcaggccg atagaggtga aatgtacaaa  2040
```

```
gattatatgc aatcggtaat tgataacccc tacttcgtag gcgcgcactg gttccagtat   2100
atggattcgc cattaacggg cagagcttat gatggtgaaa actacaatgt gggttttgtg   2160
gatgttaccg acacgccgta ccaagaaatg gtggatgcag caaaagaagt aaatgcgaaa   2220
atatacaccg aaaggctagg cagcaaataa gaattc                             2256

SEQ ID NO: 3             moltype = DNA   length = 22
FEATURE                  Location/Qualifiers
source                   1..22
                         mol_type = other DNA
                         organism = synthetic construct
SEQUENCE: 3
ggttaaagtt ggatatgcag tc                                            22

SEQ ID NO: 4             moltype = DNA   length = 19
FEATURE                  Location/Qualifiers
source                   1..19
                         mol_type = other DNA
                         organism = synthetic construct
SEQUENCE: 4
cttggactgc atatccaac                                                19

SEQ ID NO: 5             moltype = DNA   length = 22
FEATURE                  Location/Qualifiers
source                   1..22
                         mol_type = other DNA
                         organism = synthetic construct
SEQUENCE: 5
cccgatagtg gagacaacaa cg                                            22

SEQ ID NO: 6             moltype = DNA   length = 24
FEATURE                  Location/Qualifiers
source                   1..24
                         mol_type = other DNA
                         organism = synthetic construct
SEQUENCE: 6
ggcgaggttt aaatcgttgt tgtc                                          24

SEQ ID NO: 7             moltype = DNA   length = 26
FEATURE                  Location/Qualifiers
source                   1..26
                         mol_type = other DNA
                         organism = synthetic construct
SEQUENCE: 7
ccaaagttga ttacccgggt aaaatc                                        26

SEQ ID NO: 8             moltype = DNA   length = 28
FEATURE                  Location/Qualifiers
source                   1..28
                         mol_type = other DNA
                         organism = synthetic construct
SEQUENCE: 8
ctaaactatg gattttaccc gggtaatc                                      28

SEQ ID NO: 9             moltype = DNA   length = 21
FEATURE                  Location/Qualifiers
source                   1..21
                         mol_type = other DNA
                         organism = synthetic construct
SEQUENCE: 9
caagccaatg cctgatcgct c                                             21

SEQ ID NO: 10            moltype = DNA   length = 22
FEATURE                  Location/Qualifiers
source                   1..22
                         mol_type = other DNA
                         organism = synthetic construct
SEQUENCE: 10
cgccaaactt agagcgatca gg                                            22

SEQ ID NO: 11            moltype = DNA   length = 22
FEATURE                  Location/Qualifiers
source                   1..22
                         mol_type = other DNA
                         organism = synthetic construct
SEQUENCE: 11
gcagtgagcg aaaaagcttt tg                                            22

SEQ ID NO: 12            moltype = DNA   length = 21
FEATURE                  Location/Qualifiers
```

```
source                  1..21
                        mol_type = other DNA
                        organism = synthetic construct
SEQUENCE: 12
gcgcgtagca aaagcttttt c                                                    21

SEQ ID NO: 13           moltype = DNA   length = 21
FEATURE                 Location/Qualifiers
source                  1..21
                        mol_type = other DNA
                        organism = synthetic construct
SEQUENCE: 13
gagcgaaaaa tcatgggcta c                                                    21

SEQ ID NO: 14           moltype = DNA   length = 17
FEATURE                 Location/Qualifiers
source                  1..17
                        mol_type = other DNA
                        organism = synthetic construct
SEQUENCE: 14
gcgcgtagcc catgatt                                                         17

SEQ ID NO: 15           moltype = DNA   length = 22
FEATURE                 Location/Qualifiers
source                  1..22
                        mol_type = other DNA
                        organism = synthetic construct
SEQUENCE: 15
ccctctcgca cgccattata ac                                                   22

SEQ ID NO: 16           moltype = DNA   length = 23
FEATURE                 Location/Qualifiers
source                  1..23
                        mol_type = other DNA
                        organism = synthetic construct
SEQUENCE: 16
cgacggtagt tataatggcg tgc                                                  23

SEQ ID NO: 17           moltype = DNA   length = 21
FEATURE                 Location/Qualifiers
source                  1..21
                        mol_type = other DNA
                        organism = synthetic construct
SEQUENCE: 17
ggatttttgg ggcccaatgc c                                                    21

SEQ ID NO: 18           moltype = DNA   length = 22
FEATURE                 Location/Qualifiers
source                  1..22
                        mol_type = other DNA
                        organism = synthetic construct
SEQUENCE: 18
cgaatacatc tggcattggg cc                                                   22

SEQ ID NO: 19           moltype = DNA   length = 22
FEATURE                 Location/Qualifiers
source                  1..22
                        mol_type = other DNA
                        organism = synthetic construct
SEQUENCE: 19
cgacccagaa tttaaaaagc gc                                                   22

SEQ ID NO: 20           moltype = DNA   length = 23
FEATURE                 Location/Qualifiers
source                  1..23
                        mol_type = other DNA
                        organism = synthetic construct
SEQUENCE: 20
cgtttccata gcgcgctttt taa                                                  23

SEQ ID NO: 21           moltype = DNA   length = 23
FEATURE                 Location/Qualifiers
source                  1..23
                        mol_type = other DNA
                        organism = synthetic construct
SEQUENCE: 21
ctacaaagag ggcttgcaca agc                                                  23

SEQ ID NO: 22           moltype = DNA   length = 21
```

```
FEATURE              Location/Qualifiers
source               1..21
                     mol_type = other DNA
                     organism = synthetic construct
SEQUENCE: 22
gcccacttct gcttgtgcaa g                                              21

SEQ ID NO: 23        moltype = DNA  length = 25
FEATURE              Location/Qualifiers
source               1..25
                     mol_type = other DNA
                     organism = synthetic construct
SEQUENCE: 23
ggtgctatgg atcacggtat gtatc                                          25

SEQ ID NO: 24        moltype = DNA  length = 20
FEATURE              Location/Qualifiers
source               1..20
                     mol_type = other DNA
                     organism = synthetic construct
SEQUENCE: 24
ccggggtgat acataccgtg                                                20

SEQ ID NO: 25        moltype = DNA  length = 24
FEATURE              Location/Qualifiers
source               1..24
                     mol_type = other DNA
                     organism = synthetic construct
SEQUENCE: 25
ctatggatca cggttcgttt cacc                                           24

SEQ ID NO: 26        moltype = DNA  length = 26
FEATURE              Location/Qualifiers
source               1..26
                     mol_type = other DNA
                     organism = synthetic construct
SEQUENCE: 26
gtgaattaaa ccggggtgaa acgaac                                         26

SEQ ID NO: 27        moltype = DNA  length = 30
FEATURE              Location/Qualifiers
source               1..30
                     mol_type = other DNA
                     organism = synthetic construct
SEQUENCE: 27
ctggttccag tatatggatc aaccattaac                                     30

SEQ ID NO: 28        moltype = DNA  length = 23
FEATURE              Location/Qualifiers
source               1..23
                     mol_type = other DNA
                     organism = synthetic construct
SEQUENCE: 28
ctctgcccgt taatggttga tcc                                            23
```

AGARASE MUTANT WITH IMPROVED THERMAL STABILITY AND APPLICATION THEREOF

REFERENCE TO SEQUENCE LISTING

The instant application contains a Sequence Listing in XML format as a file named "YGHY-2023-04-SEQ.xml", created on Mar. 12, 2024, of 28,850 bytes in size, and which is hereby incorporated by reference in its entirety.

TECHNICAL FIELD

The present disclosure relates to an agarase mutant with improved thermal stability and application thereof, belonging to the fields of genetic engineering technology and enzyme engineering.

BACKGROUND

Red algae are the most productive of all commercial algae and are abundant in the ocean, and agar is the main component of their cell walls. Agar, as a gel and thickener, is recognized as a safe food additive and can also be applied in the pharmaceutical industry, but with low added value. The main structure of agarose is composed of repetitive β-D-galactose and 3,6-anhydrous-α-L-galactose (AHG) disaccharide units which are linked together. It has been reported that the oligosaccharides extracted from agar have various biological activities, including high antioxidant activity, anti-inflammatory activity, prebiotic effect and bacteriostatic and whitening effects, which greatly improves the added value of agar.

The methods of degrading agar to prepare oligosaccharides from agar (divided into agaro-oligosaccharides (AOS) and neoagaro-oligosaccharides (NAOS)) include physical, chemical and enzymatic hydrolysis methods, each with its own unique advantages and disadvantages. In recent years, the enzymatic hydrolysis method has become a research hotspot due to its characteristics of uniform product, simple process, low energy consumption, no pollution, etc. Therefore, enzymatic hydrolysis for producing the oligosaccharides from agar is considered to be the sustainable and most promising method for the commercial production of the oligosaccharides from agar. But when the system temperature is lower than 40° C. (sol-gel transition temperature), agar forms gel, which greatly reduces the efficiency of enzymatic hydrolysis. However, the optimal temperature for most agarases is within a range of 30-40° C., and thus their thermal stability is poor; when the system temperature is higher than 50° C., the activities of the agarases are greatly damaged; and therefore, there are great limitations in the practical industrial application of the agarases.

In the prior art, there are ways to improve the thermal stability of the agarases by means of genetic engineering.

For example, Su, Xu, Yan, Xie, and Lin et al. increased the $T50^{10}$ (temperature with a half-life of 10 min) of agarase AgaA derived from *Vibrio* sp. ZC-1 by 1.5° C. (disclosed in the paper of SU B-M, XU X-Q, YAN R-X, et al. Mutagenesis on the surface of a beta-agarase from *Vibrio* sp. ZC-1 increased its thermo-stability [J]. Enzyme and Microbial Technology, 2019, 127: 22-31.);

Jang, Lee and Kim et al. obtained a mutant E99K-T3071 with Tm increased by 5.2° C. by performing random mutagenesis on agarase AgaB derived from *Zobellia galactanivorans* (disclosed in the paper of JANG M-K, LEE S W, LEE D-G, et al. Enhancement of the thermostability of a recombinant beta-agarase, AgaB, from *Zobellia galactanivorans* by random mutagenesis [J]. Biotechnology Letters, 2010, 32(7): 943-9.);

Shi, Lu, Ma, Fu, and Yu et al. mutated agarase AgaB derived from *Pseudoalteromonas* sp. CY24 and obtained a mutant S2, whose Tm is 4.6° C. higher than that of the wild type agarase (disclosed in the paper of CHAOS, XINZHI L, CUIPING M, et al. Enhancing the thermostability of a novel beta-agarase AgaB through directed evolution [J]. Applied Biochemistry and Biotechnology, 2008, 151(1): 51-9.); and Zhang et al. modified agarase AgWH50C derived from *Agarivorans gilvus* WH0801, the obtained mutant K621F had a melting temperature (Tm) 0.88° C. higher than that of the wild type agarase, and the optimal temperature was increased from 30° C. to 38° C. (disclosed in the paper of ZHANG P, ZHANG J, ZHANG L, et al. Structure-based design of agarase AgWH50C derived from *Agarivorans gilvus* WH0801 to enhance thermostability [J]. Applied Microbiology and Biotechnology, 2019, 103(3): 1289-98.).

However, the thermal stability of the existing agarases still cannot meet the needs of industrial production. Therefore, the development of high heat-resistant agarases will significantly improve the production and application values of the agarases, and is more conducive to the industrialized production of oligosaccharides from agar, which is one of the key technologies to achieve the high value of marine resources.

SUMMARY

In the early stage, the inventors conducted researches on different agarase which were derived from different sources and produced different oligosaccharides by hydrolysis. It was found that after being combined with agarose substrate, agarase Aga50D (NCBI accession number: ABD81904, sequence as shown in SEQ ID NO. 1) derived from *Saccharophagus degradans* 2-40 had a complete crystal structure (PDB:4BQ2) and produced single neoagarobiose.

After characterizing the wild type agarase derived from *S. degradans* 2-40 and a mutant provided by the present disclosure, it was found that the single-point mutant greatly improved the heat resistance of agarase, with a maximum increase in apparent melting temperature (Tm) of 23° C., making it an agarase mutant with the largest increase in thermal stability in existing reports. Compared with the previously reported AgWH50C agarase mutant K621F derived from an *Agarivorans gilvus* WH0801 strain, the mutant provided by the present disclosure has a better heat resistance improvement effect, and the enzyme activity thereof is also improved to a certain extent, which are conducive to improving the utilization rate of agarose raw materials and increasing the yield of neoagarobiose, thus endowing agarase with greater industrial application value.

The present disclosure provides an agarase mutant with improved thermal stability, and an *Escherichia coli* engineered strain capable of expressing the agarase mutant.

The present disclosure provides an agarase mutant, which is obtained by mutating the amino acid at the $86^{th}$ site, the $373^{rd}$ site, the $374^{th}$ site, the $496^{th}$ site, the $507^{th}$ site, or the $747^{th}$ site of agarase with an amino acid sequence as shown in SEQ ID NO. 1.

In one implementation of the present disclosure, the parental enzyme agarase is derived from *S. degradans* 2-40.

In one implementation of the present disclosure, the nucleotide sequence encoding the parental enzyme agarase is as shown in SEQ ID NO. 2.

In one implementation of the present disclosure, the agarase mutant is obtained by mutating the alanine at the 86$^{th}$ site of the agarase with the amino acid sequence as shown in SEQ ID NO. 1 to aspartic acid, designated as A86D.

In one implementation of the present disclosure, the amino acid sequence of the mutant enzyme A86D is as shown in SEQ ID NO. 3.

In one implementation of the present disclosure, the nucleotide sequence encoding the mutant enzyme A86D is as shown in SEQ ID NO. 4.

In one implementation of the present disclosure, the agarase mutant is obtained by mutating the serine at the 373$^{rd}$ site of the agarase with the amino acid sequence as shown in SEQ ID NO. 1 to alanine, designated as S373A.

In one implementation of the present disclosure, the agarase mutant is obtained by mutating the phenylalanine at the 374$^{th}$ site of the agarase with the amino acid sequence as shown in SEQ ID NO. 1 to tryptophan, designated as F374W.

In one implementation of the present disclosure, the agarase mutant is obtained by mutating the alanine at the 496$^{th}$ site of the agarase with the amino acid sequence as shown in SEQ ID NO. 1 to proline, designated as A496P.

In one implementation of the present disclosure, the agarase mutant is obtained by mutating the valine at the 507$^{th}$ site of the agarase with the amino acid sequence as shown in SEQ ID NO. 1 to lysine, designated as V507K.

In one implementation of the present disclosure, the agarase mutant is obtained by mutating the serine at the 747$^{th}$ site of the agarase with the amino acid sequence as shown in SEQ ID NO. 1 to glutamine, designated as S747Q.

The present disclosure also provides a gene encoding the above agarase mutant.

The present disclosure provides a recombinant vector carrying the above gene.

In one implementation of the present disclosure, the recombinant vector uses any one of pPIc9k, pHIL-S1, pPIcza, and pET28a as an expression vector.

The present disclosure provides a recombinant cell expressing the above mutant, or containing the above gene, or containing the above recombinant vector.

In one implementation of the present disclosure, the recombinant cell takes a prokaryotic cell or a eukaryotic cell as an expression host.

In one implementation of the present disclosure, the recombinant cell uses any one of *E. coli* BL(21)DE3, *Pichia pastoris* GS115, *P. pastoris* KM71, and *P. pastoris* KM7 as an expression host.

The present disclosure provides a method for preparing the above agarase mutant, and the method includes the following steps:
(1) designing, according to a determined mutation site, a mutation primer for site-directed mutagenesis, carrying out site-directed mutagenesis with the vector carrying the gene encoding agarase as a template, and constructing the vector containing the gene encoding the mutant;
(2) transforming the vector containing the gene encoding the mutant into a microbial cell; and
(3) selecting positive clones for fermentation culture, collecting cells by centrifugation, and carrying out cell-wall breaking to obtain supernatant, i.e., a crude enzyme solution of the agarase mutant.

The present disclosure also provides a method for improving the thermal stability of agarase, and the method includes: mutating the alanine at the 86$^{th}$ site of the agarase with the amino acid sequence as shown in SEQ ID NO. 1 to aspartic acid; or mutating the serine at the 373$^{rd}$ site of the agarase with the amino acid sequence as shown in SEQ ID NO. 1 to alanine; or mutating the phenylalanine at the 374$^{th}$ site of the agarase with the amino acid sequence as shown in SEQ ID NO. 1 to tryptophan; or mutating the alanine at the 496$^{th}$ site of the agarase with the amino acid sequence as shown in SEQ ID NO. 1 to proline; or mutating the valine at the 507$^{th}$ site of the agarase with the amino acid sequence as shown in SEQ ID NO. 1 to lysine; or mutating the serine at the 747$^{th}$ site of the agarase with the amino acid sequence as shown in SEQ ID NO. 1 to glutamine.

The present disclosure also provides a method for hydrolyzing agar, which includes adding the above mutant or the above recombinant cell to a reaction system containing the agar to carry out a decomposition reaction.

The present disclosure also provides a method for preparing neoagarobiose, where the neoagarobiose is prepared by reacting with the above mutant or the above recombinant cell.

The present disclosure also provides the application of the above mutant, or the above gene, or the above recombinant vector, or the above recombinant cell in preparation of products containing the hydrolyzed agar or preparation of products containing the neoagarobiose.

The present disclosure also provides applications of the above mutant, or the above gene, or the above recombinant vector, or the above recombinant cell in the fields of industry, medicine, biochemistry, and food.

Beneficial Effects (1) The present disclosure provides the agarase mutant with improved thermal stability, belonging to the fields of genetic engineering technology and enzyme engineering. The mutant with significantly improved thermal stability is obtained by using the method provided by the present disclosure, making it an agarase mutant with the largest increase in thermal stability in existing reports. Moreover, the enzyme activity of the mutant provided by the present disclosure is improved while the thermal stability thereof is improved.
(2) The enzyme activity of the mutant A86D provided by the present disclosure is 132.55% relative to wild enzyme, the enzyme activity is slightly increased; and the mutant A86D still retains 89.91%, 63.68% and 42.15% of the original enzyme activity after being subjected to incubation at 50° C. for 15 min, 60 min and 6 h, while the wild enzyme only retain 17.14% and 10.79% of the original enzyme activity after being subjected to incubation at 50° C. for 15 min and 60 min, and the enzyme activity of the wild enzyme is completely lost after 6 h of incubation.
(3) The mutant A86D provided by the present disclosure still retains 72.18% of the original enzyme activity after being subjected to incubation at 60° C. for 180 min and still retains 30.83% of the original enzyme activity after being subjected to incubation for 6 h, while the enzyme activity of the wild enzyme is completely lost after 30 min of incubation at 60° C.
(4) Compared with the wild enzyme, the mutant A86D provided by the present disclosure shows superior heat resistance, and can be industrially produced at a higher temperature, so that the utilization rate of agar raw materials and the yield of the oligosaccharides from agar are improved, and the mutant has a good industrial application prospect.

DETAILED DESCRIPTION

Figure 1:
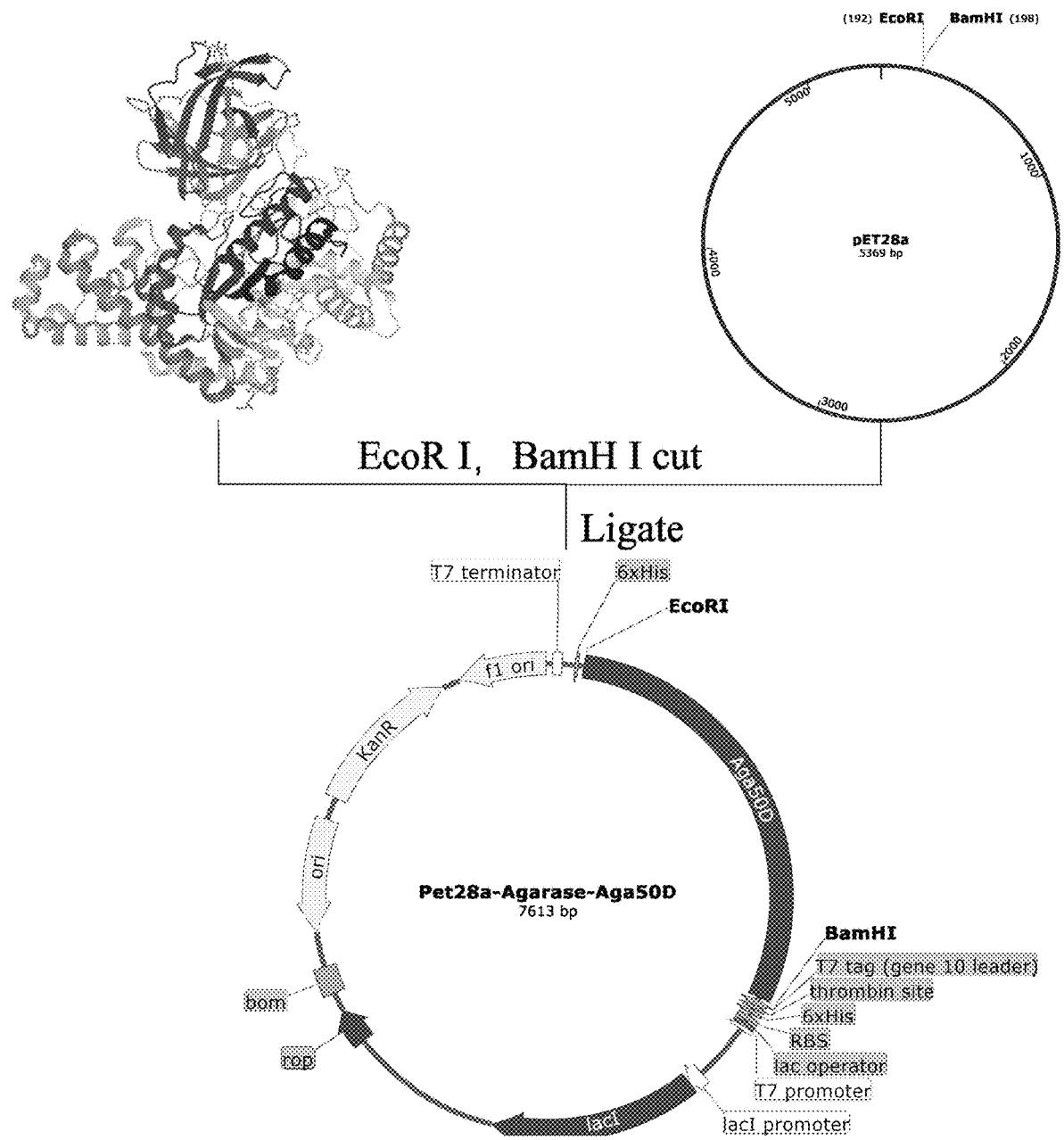
FIG. 1: Schematic diagram of plasmid construction.

The pET28a-Aga50D and its mutants involved in the following examples were synthesized by Suzhou GENEWIZ Biotechnology Co., Ltd. The main reagents involved in the following examples: a BCA concentration determination kit was purchased from Beyotime Biotechnology Co., Ltd., gene synthesis was completed by GENEWIZ Biotechnology Co., Ltd., and other commonly used reagents were domestic analytically pure reagents.

The Media Involved in the Following Examples are as Follows:

LB liquid medium: 1 g of peptone, 0.5 g of a yeast extract and 1 g of NaCl were weighed. The weighed materials were dissolved in deionized water and diluted to 100 mL, and then sterilized at 121° C. for 20 min in an autoclave.

LB solid medium: 1.8% agar powder was added to the LB liquid medium.

LB liquid-resistant medium: kanamycin was added to the LB liquid medium at a final concentration of 50 $\mu g \cdot mL^{-1}$.

LB solid medium: kanamycin was added to the LB solid medium at a final concentration of 50 $\mu g \cdot mL^{-1}$.

The Purification Method of the Enzymes Involved in the Following Examples is as Follows:

(1) Equilibration: a nickel column was equilibrated with a buffer solution which contained 50 mM of Tris-HCl and 500 mM of NaCl, and had a pH of 7.5;

(2) Sample loading: a pretreated sample was loaded at a flow rate of 1 mL/min;

(3) Washing: mixed proteins were washed with a buffer solution which contained 50 mM of Tris-HCl, 500 mM of NaCl and 20 mM of imidazole, and had a pH of 7.5; and (4) Elution: a buffer solution which contained 50 mM of Tris-HCl, 500 mM of NaCl and 300 mM of imidazole, and had a pH of 7.5 was used for elution, and a target protein was collected to obtain the purified enzyme.

The Detection Methods Involved in the Following Examples are Described Below:

Mutant Enzyme Activity Assay:

The enzyme activity was determined by using a 3,5-dinitrosalicylic acid method (DNS). Agarase catalyzed the hydrolysis of agarose under certain conditions to generate reducing sugar, and 3,5-dinitrosalicylic acid and the reducing sugar were reduced under thermal conditions so as to form a brownish red amino complex. Within a certain range, the color depth was proportional to the amount of the reducing sugar, which could be measured at a wavelength of 520 nm to calculate the enzyme activity. Definition of enzyme activity unit: the amount of enzyme required to catalyze the production of 1 μmol of D-galactose per minute at 30° C. under the condition that pH is 7.0 is defined as one activity unit.

Enzyme Activity Assay Steps:

(1) Preheating: 2 mL of a 1 $mg \cdot mL^{-1}$ agarose solution (with pH of 7.0) was taken and placed in a colorimetric tube.

(2) Reaction: 0.1 mL of an enzyme solution was added, and evenly mixed by shaking for reacting for 20 min; and 1.5 mL of DNS was added to terminate the reaction, and the product was boiled in a water bath for 5 min, and then immediately cooled.

(3) Measurement: the absorbance was measured at a wavelength of 520 nm, and the enzyme activity was calculated.

Determination of Tm Value

Differential scanning fluorometry (DSF) was used. The natural protein was in a folded state, with the hydrophobic part hidden inside. As the temperature rose, the protein structure gradually disintegrated, exposing the hydrophobic part. At this time, dyes with affinity for the hydrophobic part bound to the protein, showing an increase in the fluorescence signal intensity of the system; when the temperature reached a certain point, the unfolded protein chains aggregated, and the fluorescent dyes could not bind, and returned to the environment or were subjected to fluorescence quenching at a high temperature, resulting in a decrease in the fluorescence signal intensity; and by tracking and detecting changes in fluorescence signals, the Tm of the protein could be determined. The SYPRO Orange dye was diluted 100 times, and 5 μL of the dye was mixed with 20 μL of protein and placed in a 96-well thin-walled PCR plate. Then, in an ABI StepOnePlus real-time fluorescence quantitative PCR instrument system, the obtained mixture was heated from 25° C. to 99° C. to monitor the fluorescence change.

Steps for Determining Thermal Stability of Enzymes at 50° C. or 60° C.

(1) Preheating: 2 mL of an agarose solution (1 $mg \cdot mL^{-1}$, pH 7.0) was taken and placed in a colorimetric tube, the colorimetric tube was placed in a water bath at 50° C. or 60° C., and heat preservation was carried out for 30 min, 60 min, 90 min, 120 min, 180 min and 6 h, respectively.

(2) Reaction: 0.1 mL of an enzyme solution was added, and evenly mixed by shaking for reacting for 20 min; and 1.5 mL of DNS was added to terminate the reaction, and the product was boiled in a water bath for 5 min, and then immediately cooled.

(3) Measurement: the absorbance was measured at a wavelength of 520 nm, and the enzyme activity was calculated.

Detection Method for Neoagarobiose (NA2)

An enzymatically hydrolyzed sample and a neoagarooligosaccharide standard (purchased from Qingdao BZ Oligo Biotech Co., Ltd., with a purity greater than 98%, diluted to 1 mg·mL$^{-1}$) were tested by ion chromatography (ICS-5000, Thermo Fisher Scientific, USA) after passing through a 0.22 μm filter membrane. The detection conditions were as follows: chromatographic column: a Dionex CarboPac PA-200 anion exchange column, including an analytical column (4 mm×250 mm) and a guard column (4 mm×50 mm); a mobile phase: a 100 mmol·L$^{-1}$ NaOH solution and a 150 mmol·L$^{-1}$ NaAc solution, with a flow rate being 0.5 mL·min$^{-1}$; an amperometric detector adopted four-potential pulse amperometry for detection; and the column temperature was 30° C., and the injection volume was 2 μL.

The present disclosure will be described in detail below in conjunction with the accompanying drawings and examples.

Example 1: Construction of Mutants

The specific steps are described below.

(1) Construction of a Recombinant Vector pET28a-Aga50D Containing a Wild Type Agarase Aga50D According to *S. degradans* 2-40 published by NCBI, the nucleotide sequence encoding a parental enzyme agarase was as shown in SEQ ID NO. 2 and sent to GENEWIZ Biotechnology Co., Ltd. for gene synthesis and plasmid recombination. The vector was pET28a, and the recombinant plasmid was named pET28a-Aga50D.

(2) Construction of Recombinant Vectors Containing Mutants (as Shown in FIG. 1)

Site-directed mutagenesis primers were designed to perform site-directed mutagenesis by using the recombinant plasmid pET28a-Aga50D obtained in step (1) as a template so as to obtain recombinant plasmids pET28a-A86D, pET28a-V172N, pET28a-K259P, pET28a-S286D, pET28a-S373A, pET28a-F374W, pET28a-N400R, pET28a-A496P, pET28a-V507K, pET28a-P677H, pET28a-S705M, pET28a-Y706F, and pET28a-S747Q which contain mutants A86D, V172N, K259P, S286D, S373A, F374W, N400R, A496P, V507K, P677H, S705M, Y706F, and S747Q, respectively.

The primer sequences involved are described below.

The site-directed mutagenesis primers for introducing A86D mutation:

```
A86D-F:
                                        (SEQ ID NO: 3)
5'-GGTTAAAGTTGGATATGCAGTC-3';
and A86D-R:
                                        (SEQ ID NO: 4)
5'-CTTGGACTGCATATCCAAC-3'.
```

The site-directed mutagenesis primers for introducing V172N mutation:

```
V172N-F:
                                        (SEQ ID NO: 5)
5'-CCCGATAGTGGAGACAACAACG-3';
and V172N-R:
                                        (SEQ ID NO: 6)
5'-GGCGAGGTTTAAATCGTTGTTGTC-3'.
```

The site-directed mutagenesis primers for introducing K259P mutation:

```
K259P-F:
                                        (SEQ ID NO: 7)
5'-CCAAAGTTGATTACCCGGGTAAAATC-3';
and K259P-R:
                                        (SEQ ID NO: 8)
5'-CTAAACTATGGATTTTACCCGGGTAATC-3'.
```

The site-directed mutagenesis primers for introducing S286D mutation:

```
S286D-F:
                                        (SEQ ID NO: 9)
5'-CAAGCCAATGCCTGATCGCTC-3';
and S286D-R:
                                        (SEQ ID NO: 10)
5'-CGCCAAACTTAGAGCGATCAGG-3'.
```

The site-directed mutagenesis primers for introducing S373A mutation:

```
S373A-F:
                                        (SEQ ID NO: 11)
5'-GCAGTGAGCGAAAAAGCTTTTG-3';
and S373A-R:
                                        (SEQ ID NO: 12)
5'-GCGCGTAGCAAAAGCTTTTTC-3'.
```

The site-directed mutagenesis primers for introducing F374W mutation:

```
F374W-F:
                                        (SEQ ID NO: 13)
5'-GAGCGAAAAATCATGGGCTAC-3';
and F374W-R:
                                        (SEQ ID NO: 14)
5'-GCGCGTAGCCCATGATT-3'.
```

The site-directed mutagenesis primers for introducing N400R mutation:

```
N400R-F:
                                        (SEQ ID NO: 15)
5'-CCCTCTCGCACGCCATTATAAC-3';
and N400R-R:
                                        (SEQ ID NO: 16)
5'-CGACGGTAGTTATAATGGCGTGC-3'.
```

The site-directed mutagenesis primers for introducing A496P mutation:

```
A496P-F:
                                        (SEQ ID NO: 17)
5'-GGATTTTTGGGGCCCAATGCC-3';
and A496P-R:
                                        (SEQ ID NO: 18)
5'-CGAATACATCTGGCATTGGGCC-3'.
```

The site-directed mutagenesis primers for introducing V507K mutation:

```
V507K-F:
                               (SEQ ID NO: 19)
5'-CGACCCAGAATTTAAAAAGCGC-3';
and V507K-R:
                               (SEQ ID NO: 20)
5'-CGTTTCCATAGCGCGCTTTTTAA-3'.
```

The site-directed mutagenesis primers for introducing P677H mutation:

```
P677H-F:
                               (SEQ ID NO: 21)
5'-CTACAAAGAGGGCTTGCACAAGC-3';
and P677H-R:
                               (SEQ ID NO: 22)
5'-GCCCACTTCTGCTTGTGCAAG-3'.
```

The site-directed mutagenesis primers for introducing S705M mutation:

```
S705M-F:
                               (SEQ ID NO: 23)
5'-GGTGCTATGGATCACGGTATGTATC-3';
and S705M-R:
                               (SEQ ID NO: 24)
5'-CCGGGGTGATACATACCGTG-3'.
```

The site-directed mutagenesis primers for introducing Y706F mutation:

```
Y706F-F:
                               (SEQ ID NO: 25)
5'-CTATGGATCACGGTTCGTTTCACC-3';
and Y706F-R:
                               (SEQ ID NO: 26)
5'-GTGAATTAAACCGGGGTGAAACGAAC-3'.
```

The site-directed mutagenesis primers for introducing S747Q mutation:

```
S747Q-F:
                               (SEQ ID NO: 27)
5'-CTGGTTCCAGTATATGGATCAACCATTAAC-3';
and S747Q-R:
                               (SEQ ID NO: 28)
5'-CTCTGCCCGTTAATGGTTGATCC-3'.
```

The PCR Reaction System is as Follows:

TABLE 1

| Mutation PCR reaction system | |
| --- | --- |
| Reagent | Dosage (μL) |
| PrimerSTAR MAX | 25 |
| Upstream primer (10 μM) | 1 |
| Downstream primer (10 μM) | 1 |

TABLE 1-continued

| Mutation PCR reaction system | |
| --- | --- |
| Reagent | Dosage (μL) |
| Template (pET28a-Aga50D) | 0.5 |
| ddH$_2$O | 22.5 |

PCR reaction conditions: pre-denaturation at 95° C. for 3 min, denaturation at 95° C. for 3 min, denaturation at 95° C. for 30 s, annealing at 56° C. for 30 s, and extension at 72° C. for 3 min and 48 s, with a total of 30 cycles.

A target fragment obtained by gel recovery was transformed into *E. coli* BL21 (DE3), a kanamycin (50 μg/mL) LB plate was coated with a transformant, and the transformant was statically cultured overnight at 37° C. After the bacterial colonies grew out, the single colonies were picked and inoculated into an LB liquid medium containing kanamycin (50 μg/mL), and cultured overnight at 37° C. under the condition of 200 rpm; and the bacterial liquid was sent to GENEWIZ Biotechnology Co., Ltd. for determination. The mutant engineered strains containing the correct mutants were respectively obtained:

*E. coli* BL21 (DE3)/pET28a-A86D, *E. coli* BL21 (DE3)/pET28a-V172N, *E. coli* BL21 (DE3)/pET28a-K259P, *E. coli* BL21 (DE3)/pET28a-S286D, *E. coli* BL21 (DE3)/pET28a-S373A, *E. coli* BL21 (DE3)/pET28a-F374W, *E. coli* BL21 (DE3)/pET28a-N400R, *E. coli* BL21 (DE3)/pET28a-A496P, *E. coli* BL21 (DE3)/-V507K, *E. coli* BL21 (DE3)/pET28a-P677H, *E. coli* BL21 (DE3)/pET28a-S705M, *E. coli* BL21 (DE3)/pET28a-Y706F, and *E. coli* BL21 (DE3)/pET28a-S747Q; and according to the above method, the engineered strain *E. coli* BL21 (DE3)/pET28a-Aga50D containing the original enzyme was prepared.

The combination mutant PD1 was obtained by a combination mutation of 20 sites including A86D, V172N, K259P, V274K, S286D, A351P, A355P, S373A, F374W, A386V, N400R, A496P, V507K, S619E, H635K, P677H, H703R, S705M, Y706F and S747Q based on the pET28a-Aga50D; the primer sequence was the same as above, and the method was the same as above; and the engineered strain *E. coli* BL21 (DE3)/pET28a-A86D/V172N/K259P/V274K/S286D/A351P/A355P/S373A/F374W/A386V/N400R/A496P/V507K/S619E/H635K/P677H/H703R/S705M/Y706F/S747Q was obtained, and was named *E. coli* BL21 (DE3)/PD1.

Example 2: Purification of Enzymes and Determination of Enzymatic Properties (1) Production of Enzymes by Shake-Flask Fermentation The genetically engineered strains obtained in Example 1 were respectively streaked on the kanamycin (50 μg/mL) LB plate, and cultured at 37° C. for 12 h; then, single colonies were picked and inoculated into an LB liquid medium containing kanamycin (50 μg/mL) for shake-flask fermentation; and the product was cultured at 37°C for 12 h under the condition of 200 rpm so as to obtain seed liquid.

1 mL of the seed liquid was absorbed and transferred to an LB liquid medium containing 100 ml of kanamycin (50 μg/mL) for shake-flask fermentation, and then was cultured at 37° C. until OD$_{600}$ reached 0.6-0.8; and IPTG with a final concentration of 0.5 mM was added, the mixture was cooled to 16° C., enzyme was then induced, the product was centrifuged after being cultured for 12 h, and bacterial cells were collected.

(2) Purification of Enzymes

Figure 4:
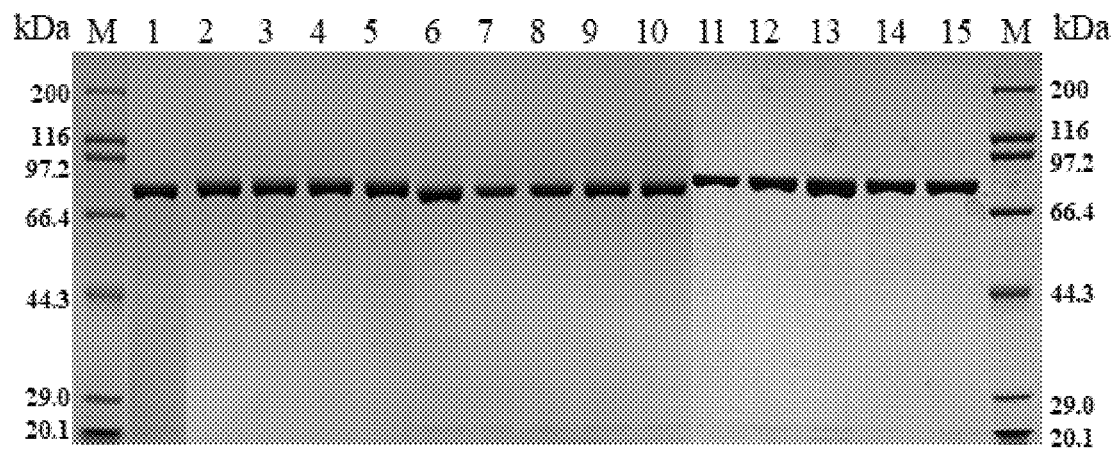
FIG. 4: SDS-PAGE images of a wild enzyme Aga50D and its mutants after purification; and in the figure, M represents protein molecular weight standard, 1 represents the purified wild type Aga50D, and 2-15 represent the purified mutants, which are PD1, A86D, V172N, K259P, S286D, S373A, F374W, N400R, A496P, V507K, P677H, S705M, Y706F, and S747Q in sequence.

An appropriate amount (2-3 times the volume) of a lysis buffer solution (containing 50 mmol/L Tris HCl and 100 mmol/L NaCl, with a pH of 7.5) was added into the centrifugally collected bacterial cells for resuspending the bacterial cells. The product was subjected to ultrasonication on ice for 15-20 min at a power of 30%; then, the ultrasonication was performed for 2 s, and stopped for 3 s; after the ultrasonication was finished, the product was centrifuged at 4° C. for 10 min under the condition of 8000 rpm to collect supernatant, and the supernatant was filtered through a 0.22 µm filter membrane. $Ni^{2+}$ column affinity chromatography purification was performed to obtain mutant enzymes. After enzyme activity assay and SDS-PAGE electrophoresis detection, the results are as shown in FIG. 4.

Pure enzyme solutions containing wild type agarase and its mutant enzymes A86D, V172N, K259P, S286D, S373A, F374W, N400R, A496P, V507K, P677H, S705M, Y706F, S747Q, and PD1 were prepared, respectively.

(3) Enzyme Activity Assay

Figure 2:
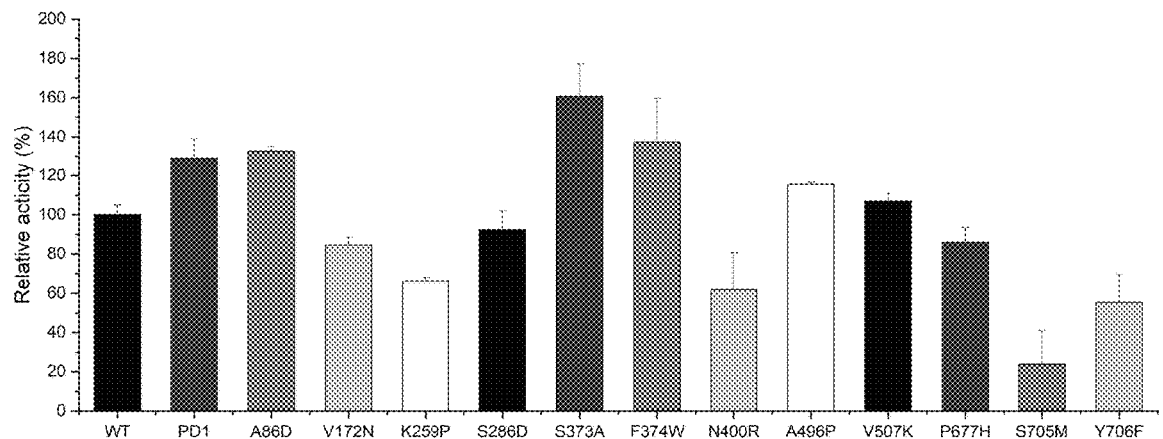
FIG. 2: Enzyme activity characterization of a wild enzyme Aga50D and its mutants.

The enzyme activities of the above wild type agarase and its mutant enzymes A86D, V172N, K259P, S286D, S373A, F374W, N400R, A496P, V507K, P677H, S705M, Y706F, S747Q and PD1 were determined. The enzyme activity of the wild type agarase was defined as 100%, and the relative enzyme activities of the mutant enzymes was detected. The results are as shown in Table 2 and FIG. 2.

TABLE 2

Relative enzyme activities of a wild type enzyme and its mutants

| Enzyme | Tm | ΔTm | Relative enzyme activity (%) |
|---|---|---|---|
| WT | 41.974 | — | 100 |
| PD1 | 48.802 | 6.828 | 129.1 ± 9.9 |
| A86D | 65.176 | 23.202 | 132.6 ± 2.5 |
| V172N | 42.768 | 0.793 | 84.6 ± 4.1 |
| K259P | 42.487 | 0.513 | 66.3 ± 1.8 |
| S286D | 43.196 | 1.221 | 92.4 ± 9.8 |
| S373A | 41.987 | 0.013 | 160.7 ± 6.3 |
| F374W | 42.677 | 0.703 | 137.3 ± 10.6 |
| N400R | 43.202 | 1.227 | 61.9 ± 9.7 |
| A496P | 42.210 | 0.236 | 115.5 ± 1.1 |
| V507K | 42.615 | 0.641 | 107.0 ± 3.8 |
| P677H | 44.043 | 2.069 | 86.0 ± 7.4 |
| S705M | 44.137 | 2.163 | 23.8 ± 7.0 |
| Y706F | 43.638 | 1.664 | 55.4 ± 10.4 |
| S747Q | 47.651 | 5.677 | 141.1 ± 4.5 |

Figure 3:
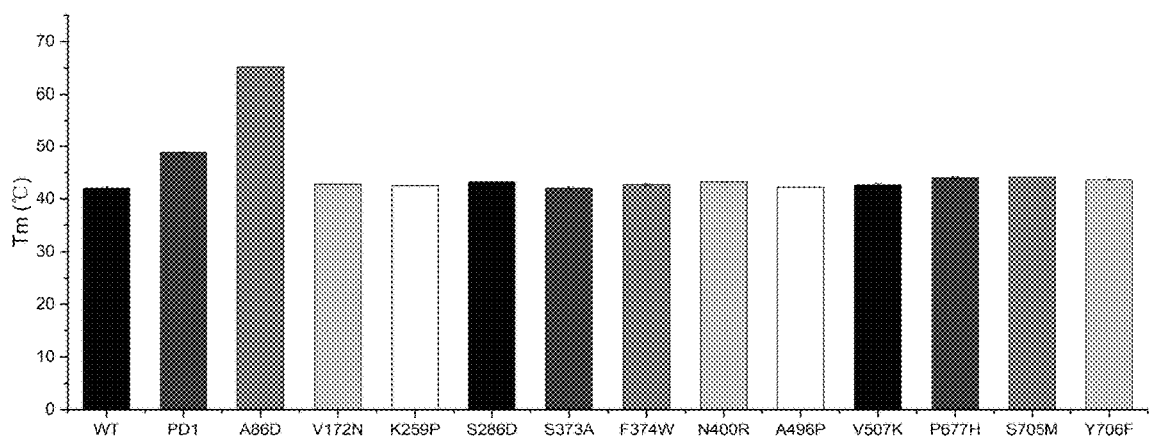
FIG. 3: Tm characterization of a wild enzyme Aga50D and its mutants.

The results show that the Tm values of the wild type agarase and its mutant enzymes PD1, A86D, V172N, K259P, S286D, S373A, F374W, N400R, A496P, V507K, P677H, S705M, Y706F, and S747Q are determined by differential scanning fluorometry, with PD1 (ΔTm=6.828° C.), S747Q (ΔTm=5.677° C.), S705M (ΔTm=2.163° C.), and P677H (ΔTm=2.069° C.) being significant in effect. It is worth noting that the thermal melting temperature (Tm=65.176° C., ΔTm=23.202° C.) of A86D is much higher than that of the wild type agarase (Tm=41.974° C.), so that the heat resistance is greatly improved, as shown in Table 2 and FIG. 3.

Although the enzyme activities of S373A, F374W and A496P have been improved, the increase of their thermal melting temperature is not significant.

Based on the relative enzyme activities, the mutants PD1, A86D, and S747Q with superior overall performance were selected for subsequent experiments.

(4) Enzyme Thermal Stability at 50° C.

Figure 5:
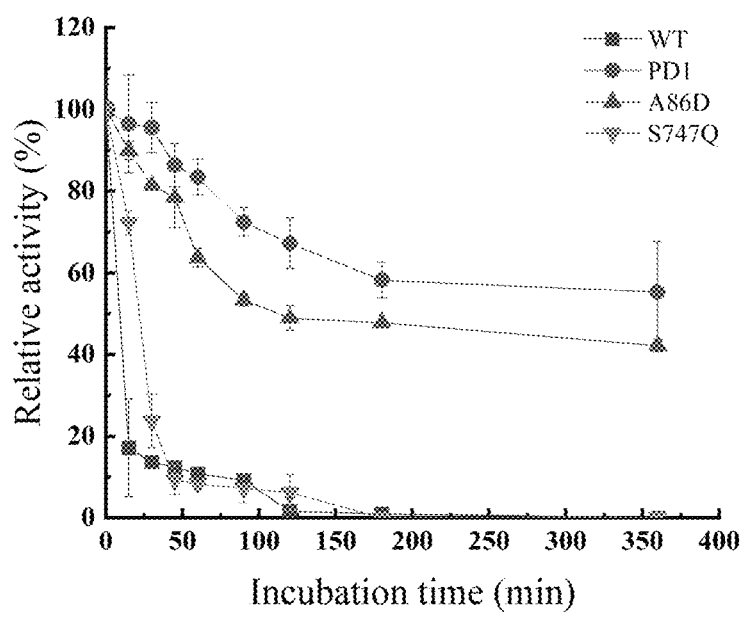
FIG. 5: Thermal stability characterization of a wild enzyme Aga50D and its mutants at 50° C.

The results of an enzyme thermal stability experiment at 50° C. are as shown in FIG. 5.

The results showed that the heat resistance of the mutant A86D was significantly enhanced.

At 50° C., the experimental results showed that the wild enzyme Aga50D only retained 13.65% of the original enzyme activity after being subjected to incubation for 30 min, only retained 10.79% of the original enzyme activity after being subjected to incubation for 60 min, and almost lost all enzyme activity after being subjected to incubation for 180 min.

At 50° C., the mutant S747Q retained 72.17% of the original enzyme activity after being subjected to incubation for 15 min, retained 23.71% of the original enzyme activity after being subjected to incubation for 30 min, and was completely inactivated after being subjected to incubation for 180 min.

At 50° C., the mutant A86D retained 81.39% of the original enzyme activity after being subjected to incubation for 30 min, retained 63.68% of the original enzyme activity after being subjected to incubation for 60 min, and still retained 42.15% of the original enzyme activity after being subjected to incubation for 6 h.

At 50° C., the mutant PD1 retained 95.51% of the original enzyme activity after being subjected to incubation for 30 min, retained 83.37% of the original enzyme activity after being subjected to incubation for 60 min, and still retained 55.28% of the original enzyme activity after being subjected to incubation for 6 h.

Therefore, a heat resistance test at 60° C. was additionally performed to further explore the superior heat resistance performance of PD1 and A86D.

(5) Enzyme Thermal Stability at 60° C.

Figure 6:
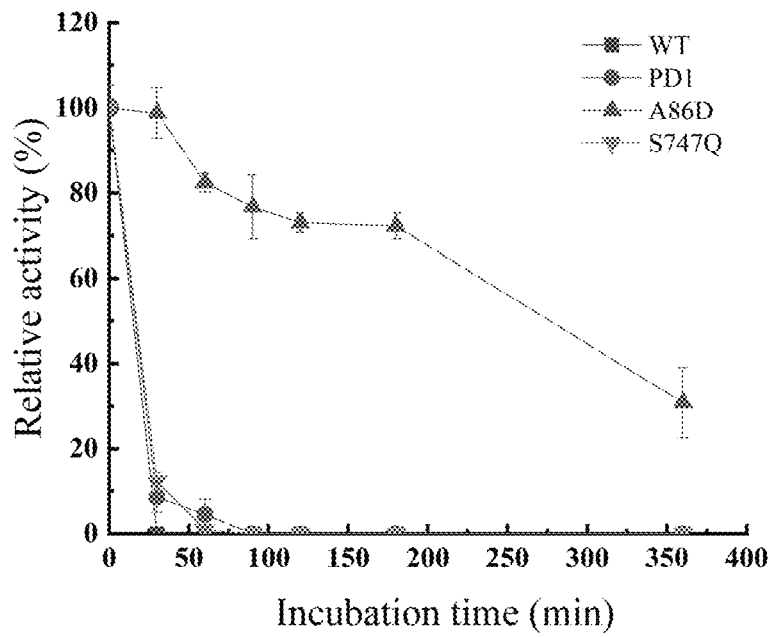
FIG. 6: Thermal stability characterization of a wild enzyme Aga50D and its mutants at 60° C.

The results of an enzyme thermal stability experiment at 60° C. are as shown in FIG. 6.

The results showed that the heat resistance of the mutant A86D was significantly enhanced.

At 60° C., the experimental results showed that the wild enzyme Aga50D had poor heat resistance, and was completely inactivated after being subjected to incubation at 60° C. for 30 min.

At 60° C., the mutant S747Q retained 12.26% of the original enzyme activity after being subjected to incubation for 30 min, only retained 0.94% of the original enzyme activity after being subjected to incubation for 60 min, and was completely inactivated after being subjected to incubation for 90 min.

At 60° C., the mutant PD1 retained 8.50% of the original enzyme activity after being subjected to incubation for 30 min, only retained 4.50% of the original enzyme activity after being subjected to incubation for 60 min, and was completely inactivated after being subjected to incubation for 90 min.

At 60° C., the mutant A86D retained 98.75% of the original enzyme activity after being subjected to incubation for 30 min, retained 82.46% of the original enzyme activity after being subjected to incubation for 60 min, retained 72.18% of the original enzyme activity after being subjected to incubation for 180 min, and still retained 30.83% of the original enzyme activity after being subjected to incubation for 6 h, thus showing extremely superior heat resistance and having excellent industrial application potential.

Figure 7:
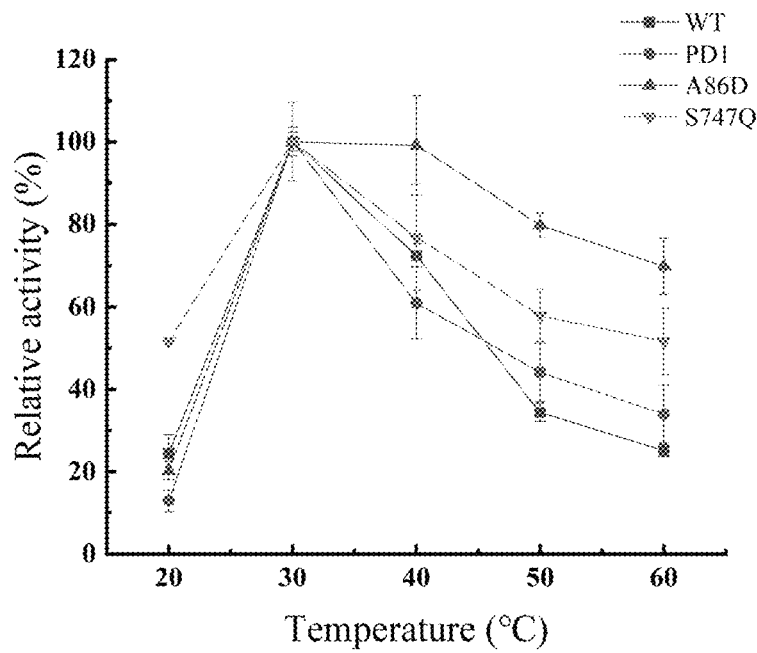
FIG. 7: Characterization of optimal reaction temperature for a wild enzyme Aga50D and its mutants.

Example 3: Determination of Enzymatic Properties (1) Optimal Reaction Temperature In order to further explore the characteristics of mutant enzymes, the enzymatic properties of PD1, A86D and S747Q were further studied. A 0.1% agarose substrate was prepared by using a buffer solution which contained Tris-HCl and had a pH of 7, and an enzyme solution with a final concentration of 0.2 mg·mL$^{-1}$ was added to react for 20 min at different temperatures so as to measure the enzyme activity. It can be seen from FIG. 7 that the optimal reaction temperature for both a wild enzyme and its mutants is 30° C.

(2) Optimal Reaction pH

Figure 8:
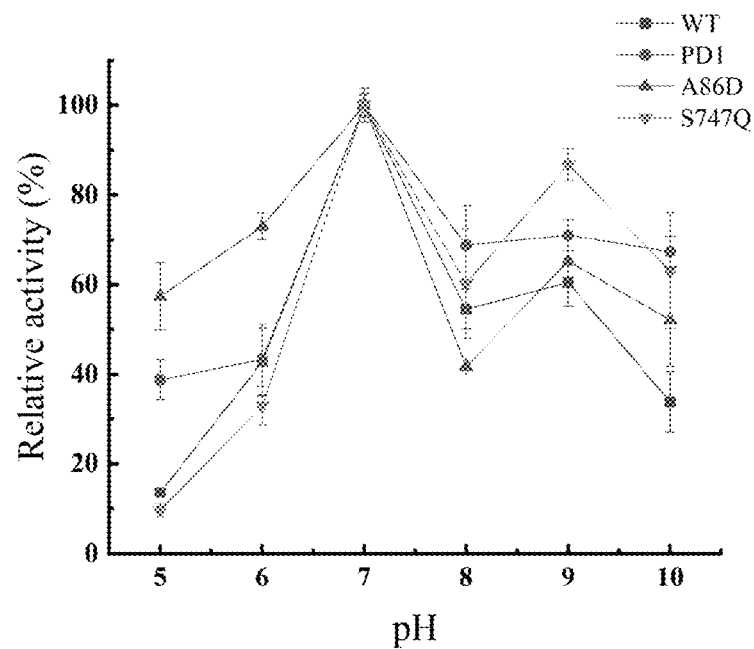
FIG. 8: Optimal reaction pH characterization of a wild enzyme Aga50D and its mutants.

A 1 mg·mL$^{-1}$ agarose substrate having a pH within a range of 5-6 was prepared by using a buffer solution containing 50 mM of citric acid, a 0.1% agarose substrate having a pH within a range of 7-8 was prepared by using a buffer solution containing 50 mM of Tris-HCl, and a 0.1% agarose substrate having a pH within a range of 9-10 was prepared by using a glycine-NaOH buffer solution. An enzyme solution with a final concentration of 0.2 mg·mL$^{-1}$ was added to react for 20 min at different temperatures so as to measure the enzyme activity. It can be seen from FIG. 8 that the optimal reaction pH for both a wild enzyme and its mutants is 7, and their properties are similar.

(3) Kinetic Parameters

Figure 9:
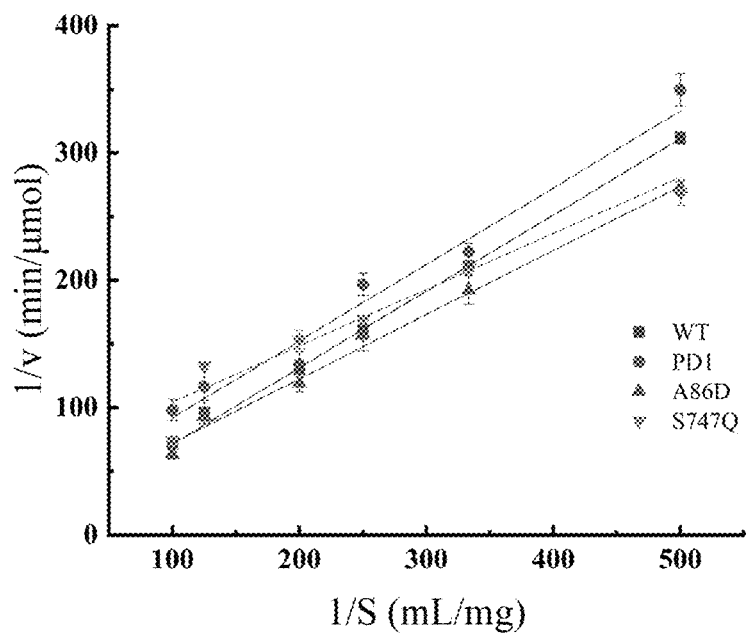
FIG. 9: Characterization of kinetic parameters of a wild enzyme Aga50D and its mutants.

Agarose substrates with concentrations of 1 mg·mL$^{-1}$, 2 mg·mL$^{-1}$, 3 mg·mL$^{-1}$, 4 mg·mL$^{-1}$, 5 mg·mL$^{-1}$, 8 mg·mL$^{-1}$ and 10 mg·mL$^{-1}$ were respectively prepared by using a buffer solution which contained Tris-HCl and had a pH of 7. An enzyme solution with a final concentration of 0.2 mg·mL$^{-1}$ was added to react under the optimal reaction conditions, and then the amount of reducing sugar produced was determined and plotted according to a Lineweaver-Burk method (FIG. 9). The linear fitting equations for the 4 curves in the figure are y=589.92x+15.37 (WT), y=621.46x+31.568 (PD1), y=506.45x+22.215 (A86D), and y=436.23x+58.247 (S747Q), respectively. Thus, various kinetic parameters of a wild enzyme and its mutants can be deduced (Table 3).

The kinetic parameters of a wild enzyme and its mutants under optimal reaction conditions are listed in Table 3.

TABLE 3

Kinetic parameters of wild type Aga50D and its mutants

|      | Km (mg/ml) | Kcat/Km (mL/mg·s) |
|------|------------|-------------------|
| WT   | 38.381     | 0.139             |
| PD1  | 19.686     | 0.154             |
| A86D | 22.794     | 0.162             |
| S747Q| 7.489      | 0.181             |

It can be seen from the data in the table that the Km values of mutants are lower than that of WT, indicating that the binding ability of the mutants to an agarose substrate is significantly increased, which is consistent with the previous conclusion about the relative enzyme activity. The Kcat/Km values of the mutants are greater than that of the WT, indicating that the catalytic ability of the mutants is improved.

Example 4: Application of Enzymes

After a 1 mg·mL$^{-1}$ agarose substrate solution was prepared by using ultrapure water, the mutant and wild type pure enzyme solutions (0.2 mg·mL$^{-1}$ enzyme solution (9.528 U·mg$^{-1}$)) prepared in step (2) of Example 2 were respectively added to react in a water bath shaker at 50° C., with a rotational speed of 200 rpm and a reaction time of 1-3 h. After the reaction was completed, a boiling water bath was used to terminate the reaction.

Part of the reaction solution was taken out every 1 h, 2 h and 3 h, unreacted polysaccharides in the reaction solution was removed by centrifugation, and supernatant was taken to obtain enzymatic hydrolysate samples: neoagarobiose (NA2). The contents of the neoagarobiose (NA2) in the above-obtained products were detected, respectively.

Figure 10:
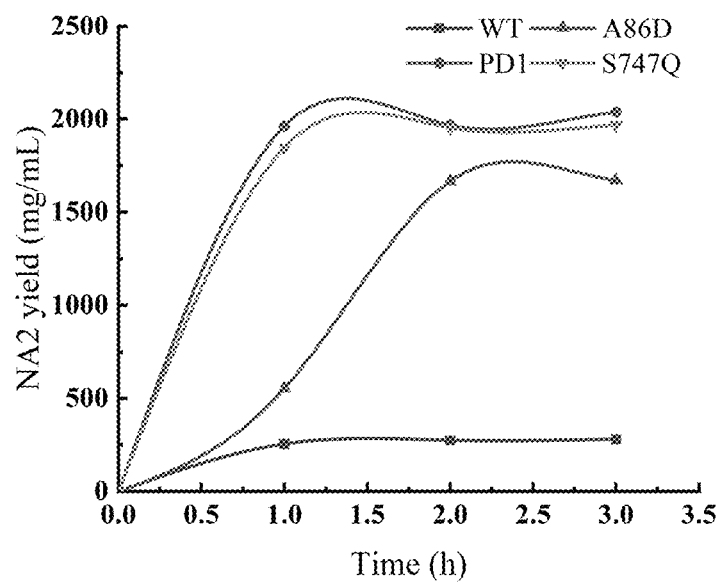
FIG. 10: Analysis on products of a wild enzyme Aga50D and its mutant at 50° C.

The results show (as shown in FIG. 10) that at 50° C., neoagarobiose produced by hydrolyzing agarose with a wild type enzyme is low in yield, which is presumed to be due to heat instability, and rapid heat inactivation; while mutant enzymes PD1, A86D, and S747Q have certain heat resistance, and can still play a catalytic role under high temperature conditions; and an agarose substrate is still in a solution state at 50° C., which promotes the binding of the substrate to the enzyme, thus further improving the yield of the neoagarobiose.

The hydrolysis reaction lasted for 3 h, and the yield of the product neoagarobiose (NA2) obtained by hydrolyzing agarose with the wild type enzyme was 278.678 mg/ml (859.3 μM);

the yield of the product neoagarobiose (NA2) obtained by hydrolyzing agarose with the mutant enzyme PD1 was 2036.281 mg/mL (6279.3 μM);

the yield of the product neoagarobiose (NA2) obtained by hydrolyzing agarose with the mutant enzyme A86D was 1670.887 mg/ml (5152.6 μM); and the yield of the product neoagarobiose (NA2) obtained by hydrolyzing agarose with the mutant enzyme S747Q was 1965.719 mg/ml (6061.7 μM).

Under the condition of 50° C., the mutant enzymes show excellent hydrolysis efficiency due to its superior heat resistance, thus greatly improving the yield of neoagarobiose, and having good industrial application value.

Example 5: Application of Enzymes

After a 1 mg·mL$^{-1}$ agarose substrate solution was prepared by using ultrapure water, the mutant and wild type pure enzyme solutions (0.2 mg·mL$^{-1}$ enzyme solution (9.528 U·mg$^{-1}$)) prepared in step (2) of Example 2 were respectively added to react in a water bath shaker at 60° C., with a rotational speed of 200 rpm and a reaction time of 1-3 h. After the reaction was completed, a boiling water bath was used to terminate the reaction.

Part of the reaction solution was taken out every 1 h, 2 h and 3 h, unreacted polysaccharides in the reaction solution was removed by centrifugation, and supernatant was taken to obtain enzymatic hydrolysate samples: neoagarobiose (NA2). The contents of the neoagarobiose (NA2) in the above-obtained products were detected, respectively.

Figure 11:
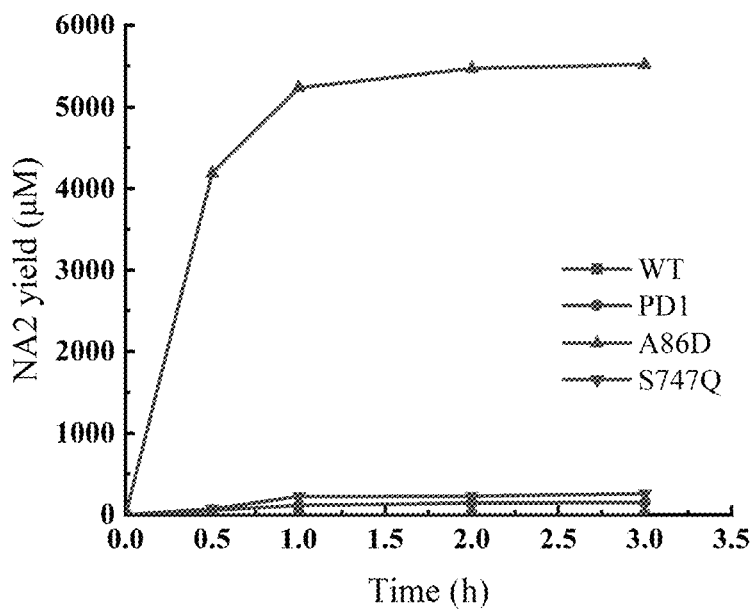
FIG. 11: Analysis on products of a wild enzyme Aga50D and its mutant at 60° C.

The results show (as shown in FIG. 11) that under the condition of 60° C., due to the heat instability and rapid inactivation of the wild type enzyme, no product neoagarobiose (NA2) is detected; and the mutants PD1 and S747Q fail to withstand the high temperature of 60° C., resulting in a large loss of enzyme activity. However, A86D can withstand a high temperature of 60° C., and still retains better enzyme activity at 60° C.; and an agarose substrate is still in a solution state at 60° C., which promotes the binding of the substrate to the enzyme, thus further improving the yield of the neoagarobiose.

The hydrolysis reaction lasted for 3 h, and the yield of the product neoagarobiose (NA2) obtained by hydrolyzing agarose with the wild type enzyme was 0 µM;

the yield of the product neoagarobiose (NA2) obtained by hydrolyzing agarose with the mutant enzyme PD1 was 147.6 µM;

the yield of the product neoagarobiose (NA2) obtained by hydrolyzing agarose with the mutant enzyme S747Q was 254.9 µM; and the yield of the product neoagarobiose (NA2) obtained by hydrolyzing agarose with the mutant enzyme A86D was 5513.6 µM.

Under the condition of 60° C., the mutant enzyme A86D shows excellent hydrolysis efficiency due to its superior heat resistance, thus greatly improving the yield of neoagarobiose, and having good industrial application value.

Although the present disclosure has been disclosed as above in exemplary embodiments, it is not intended to limit the present disclosure. Anyone familiar with this technology can make various changes and modifications without departing from the spirit and scope of the present disclosure. Therefore, the protection scope of the present disclosure shall be as defined in the Claims.

What is claimed is:

1. An agarase mutant comprising the amino acid sequence as set forth in SEQ ID NO:1 and having substitutions selected from the group consisting of: Ala86Asp, Ser373Ala, Phe374Trp, Ala496Pro, Val507Lys and Ser747Gln.

2. A recombinant cell expressing the agarase mutant according to claim 1, or containing a gene encoding the agarase mutant, or containing a recombinant vector carrying a gene encoding the agarase mutant.

3. The recombinant cell according to claim 2, wherein the recombinant cell is a prokaryotic host cell or a eukaryotic host cell.

4. A method for preparing neoagarobiose, wherein the neoagarobiose is prepared by hydrolyzing agarose with the agarase mutant according to claim 1.

* * * * *